United States Patent [19]

Briody et al.

[11] 4,289,593

[45] Sep. 15, 1981

[54] METHOD FOR INCREASING THE ULTRA-VIOLET LIGHT TRANSMITTANCE OF ETHYLENE GLYCOL

[75] Inventors: Robert G. Briody; Frances M. Cummings, both of Corpus Christi, Tex.

[73] Assignee: PPG Industries, Inc., Pittsburgh, Pa.

[21] Appl. No.: 127,292

[22] Filed: Mar. 5, 1980

Related U.S. Application Data

[63] Continuation-in-part of Ser. No. 25,306, Mar. 30, 1979, abandoned.

[51] Int. Cl.³ .............................................. C07C 31/20
[52] U.S. Cl. .................................. 204/158 R; 568/852
[58] Field of Search .................... 204/158 R; 568/868, 568/871

[56] References Cited

U.S. PATENT DOCUMENTS 3,970,711  7/1976  Reiche et al. ........................ 568/868
4,045,316  8/1977  Legan ............................ 204/158 R

FOREIGN PATENT DOCUMENTS 41-11848  6/1966  Japan .................................. 568/868

OTHER PUBLICATIONS

Van der Linde et al., "Photochem. Photobiol.", vol. 13, pp. 147-155 (1971).
Armstrong et al., "Nature", No. 5048, pp. 481-484, Jul. 30, 1966.

Primary Examiner—Joseph E. Evans
Attorney, Agent, or Firm—Edward J. Whitfield; Robert J. Grassi

[57] ABSTRACT

The ultraviolet light transmittance of ethylene glycol containing ultraviolet light absorbing impurities is increased by exposing the ethylene glycol to ultraviolet radiation at a wavelength of at least 220 nanometers from a controllable ultraviolet radiation emission source.

4 Claims, No Drawings

METHOD FOR INCREASING THE ULTRA-VIOLET LIGHT TRANSMITTANCE OF ETHYLENE GLYCOL

CROSS-REFERENCE TO RELATED APPLICATIONS

This application is a continuation-in-part of Application Ser. No. 25,306 filed Mar. 30, 1979 now abandoned.

BACKGROUND OF THE INVENTION

In a typical process for the production of ethylene glycol, ethylene oxide is hydrolyzed with water at elevated temperature and pressure, the ethylene oxide being typically produced by direct oxidation of ethylene with air or elemental oxygen in the presence of a catalyst, typically a silver-containing catalyst at elevated temperature and pressure.

The glycol stream resulting from the reaction of ethylene oxide with water is passed through evaporator means wherein the glycol is concentrated and the concentrated glycol is passed through fractioning means wherein remaining water is removed and monoethylene glycol, diethylene glycol and triethylene glycol are separated each from the other.

Glycols produced by this process often have ultraviolet light absorption characteristics which render them unsuitable for use in the manufacture of polyester fibers due to impurities which absorb ultraviolet radiation, which impurities can only be removed with difficulty by further processing such as for example, distillation. A typical specification for fiber grade monoethylene glycol requires that the glycol have ultraviolet transmittances of at least 70, 90, 95, and 98 percent at 220, 250, 275, and 350 nanometers respectively.

The nature of these ultraviolet light absorbing impurities and the mechanism by which they are formed is open to conjecture. In for example, U.S. Pat. No. 3,970,711 impurities identified as mesityl oxide and ethylene carbonate are believed to result from the feeding and subsequent hydrolysis of stripper bottoms from the ethylene oxide purification system to the glycol reaction system. It has also been found that hydrolysis of ethylene oxide stripper bottoms form quantities of crotonaldehyde and 2,4-hexadienal. Moreover ultraviolet light absorbing impurities are also believed to be formed directly from the hydrolysis of ethylene oxide with water to produce ethylene glycol.

The aforementioned U.S. Pat. No. 3,970,711 also describes means of reducing the level of impurities in the product glycol by treating the glycol containing stripper bottoms from the ethylene oxide purification system with an adsorbent material e.g. activated carbon, prior to feeding the stripper bottoms to the glycol system. Although this process could be effective in removing impurities contained in the ethylene oxide stripper bottoms, it would not remove any impurities formed directly in the hydrolysis of ethylene oxide with water.

SUMMARY OF THE INVENTION

The ultraviolet light transmittance of ethylene glycol containing ultraviolet light absorbing impurities is increased by exposing the ethylene glycol to ultraviolet radiation at a wavelength of at least 220 nanometers from a controllable ultraviolet radiation emission source.

DESCRIPTION OF THE INVENTION

In accordance with this invention, it has been found that the ultraviolet light transmittance of ethylene glycol that contains ultraviolet absorbing impurities is increased by exposing the ethylene glycol to ultraviolet radiation at a wavelength of at least 220 nanometers from a controllable ultraviolet radiation emission source. The process of the invention is particularly applicable to treating ethylene glycol having ultraviolet light absorption characteristics unsuitable for use in the manufacture of polyester fiber so as to produce ethylene glycol having ultraviolet light absorption characteristics suitable for use in the manufacture of polyester fiber.

Although the chemical nature of the impurities cannot be specified with particularity, one of their physical characteristics is their ability to absorb ultraviolet light at specific wave lengths. It is believed that this ultraviolet light absorbing capability is inherent in their chemical structure and is probably due to conjugation of two or more double bonds in the molecule. These impurities absorb ultraviolet light at wave lengths above 220 nanometers, and appear to have the strongest absorption characteristics in the range of 240 to 280 nanometers. It is postulated that treatment, according to this invention, selectively converts the chemical structure of these impurities to some form which does not have the characteristic conjugation of two or more double bonds while not causing any appreciable decomposition of the ethylene glycol, itself.

For purposes of this invention, ultraviolet light transmittance is defined as the percent transmittance of ultraviolet light through ethylene glycol over wave lengths in the range of 220 to 350 nanometers, particularly at 220, 250, 275 and 350 nanometers as compared with ultraviolet light transmittance of distilled water at the same wave length. The percent transmittance may be measured in conventional fashion by, for example, spectrophotometric means in a manner well known to the art. Further in this regard during exposure of samples to ultraviolet radiation during the course of spectrophotometric analysis, no improvement in transmittance was observed. It this regard, improvement in ultraviolet transmittance would not be expected to be observed during the course of analytical measurement since exposure time is minimal and the ultraviolet light source is of relatively low power.

In accordance with this invention, ethylene glycol e.g., monoethylene glycol containing ultraviolet absorbing impurities is exposed to a source of ultraviolet radiation e.g., a high or low pressure mercury vapor lamp, for a time sufficient to obtain the desired ultraviolet transmittance characteristics. Irradiation of the glycol may be effected by immersing the ultraviolet source e.g., one or more mercury vapor lamps in a body of glycol with continuous stirring so as to uniformly expose the glycol to ultraviolet radiation. Alternatively, the glycol may be flowed past the source of ultraviolet radiation.

Optimization of the process of the invention is, to some extent, empirical and would depend, for example, on the quantity and quality of glycol undergoing treatment, the power output of the ultraviolet source, and whether a continuous or batch treatment system is used. It is believed however that straight-forward laboratory testing would enable one skilled in the art to optimize the process of the invention for commercial use, since effectiveness of the process of the invention is readily determined simply by measuring the ultraviolet light transmittance of the irradiated glycol.

Either commercially available high pressure or low pressure mercury vapor lamps may be used as an ultraviolet source in accordance with the invention. A high pressure mercury vapor lamp emits radiation in the visible and infra-red spectra in addition to the ultraviolet spectrum whereas a low pressure mercury vapor lamp emits almost exclusively in the ultraviolet spectrum with only a small amount of visible light emissions. Since only ultraviolet radiation has been found effective in reducing the effect of ultraviolet absorbing impurities in ethylene glycol, a low pressure mercury lamp would probably be more effective and economical to operate.

Overly prolonged irradiation of the glycol, especially at the shorter, more energetic, wave lengths, i.e., appreciably less than about 220, e.g., 185 nanometers, should be avoided, since the same could result in degradation of the glycol and the formation of undesirable amounts of aldehydes. Consequently in a preferred practice of the invention, an ultraviolet source emitting at a wave length of at least about 220 nanometers, preferably at least about 240 nanometers is used. When employing high or low pressure mercury vapor lamps as an ultraviolet light source, the lower wave lengths may be screened-out by suitable filter means. One such filter means that has been found to be particularly effective is a type of glass commercially available under the tradename Vycor ®. Alternatively the filter means could be in the form of a solution of, for example, an inorganic salt dissolved in a suitable solvent capable of absorbing the shorter ultraviolet wave lengths, which solution could be circulated around the mercury lamp. Use of a solution filter could afford the additional advantage of removing the heat generated by the lamp, particularly in the case of high wattage lamps.

The effectiveness of the process of the invention does not appear to be temperature dependent, at least over a moderate range of temperature, satisfactory results having been obtained at temperatures ranging from ambient to about 60° C. It has been observed that upon heating a sample of ethylene glycol, treated in accordance with this invention, to 175° C., the ultraviolet light transmittance of the heated material decreased. This, however, is not believed attributable to "reforming" of the original ultraviolet light aborbing impurities, but rather is believed attributable to the formation of other ultraviolet light absorbing impurities caused by thermal conversion of trace impurities that would not ordinarily absorb ultraviolet light. In other words, ordinarily non-ultraviolet light absorbing impurities may be converted to ultraviolet light absorbing impurities at elevated temperature. Nevertheless, treatment of the heated glycol, in accordance with this invention, is also effective in rendering these latter impurities non-ultraviolet light absorbing.

Although the process of the invention is particularly applicable to improving the ultraviolet light transmittance of end-product ethylene glycol, e.g. monoethylene glycol, produced by the hydrolysis of ethylene oxide, the invention is equally applicable to treating ethylene glycol produced by any process which might produce a product containing ultraviolet light absorbing impurities. In addition the process of the invention is not limited to the treatment of the end-product ethylene glycol but may be employed at any stage in the production process subsequent to the hydrolysis of ethylene oxide. For example, the dilute glycol prior to evaporation may be irradiated; or the irradiation treatment may be employed at both these stages, although the same might be disadvantageous due to the necessarily larger volumes of liquid that would need to be irradiated.

The invention is further illustrated but is not intended to be limited by the following examples:

EXAMPLE 1

A 15.0×7.5 centimeter petri dish was filled to depth of 2.54 centimeters with industrial grade monoethylene glycol. An ultraviolet light source, i.e., a 450 watt, high pressurized mercury vapor lamp was centered over the dish at a distance of 19 centimeters from the surface of the glycol. The lamp was turned on and the glycol was irradiated for 60 minutes, a sample having been withdrawn after 30 minutes.

The ultraviolet light transmittances of the untreated and irradiated samples as compared to distilled water were measured at 25° C. on a Beckman Model DK-W recording spectrophotometer at 220, 250, 275 and 350 nanometers, with the following results:

|  | UV TRANSMITTANCE, % | | | |
|---|---|---|---|---|
|  | 220 nm | 250 nm | 275 nm | 350 nm |
| Fiber Grade Specification | 70 | 90 | 95 | 98 |
| Untreated | 39 | 74 | 84 | 100 |
| Irradiation, 30 mins. | 67 | 91 | 95 | 100 |
| Irradiation, 60 mins. | 76 | 94 | 95 | 100 |

EXAMPLE 2

About 10.6 liters of industrial grade monoethylene glycol was placed in a glass battery jar provided with a tight-fitting plastic cover the cover having apertures formed therein for the accommodation of an ultraviolet lamp and a sample withdrawal tube. The lamp, a 450-watt high pressure, mercury vapor lamp in a water-cooled immersion well provided with a Vycor filter was allowed to warm up for about 10 minutes and was lowered into the glycol which was continuously stirred via a magnetic stirrer. Samples of the glycol were withdrawn at intervals of 1, 2, and 3 minutes irradiation. The ultraviolet light transmittance of the untreated and irradiated glycol compared to distilled water was measured in a Beckman Model 26 recording spectrophotometer at 220, 250, 260, 275 and 350 namometers with the following results:

|  | UV TRANSMITTANCE, % | | | | |
|---|---|---|---|---|---|
|  | 220 nm | 250 nm | 260 nm | 275 nm | 350 nm |
| Untreated | 85.4 | 85.0 | 87.1 | 90.9 | 100 |
| Irradiation, 1 min. | 86.0 | 91.0 | 94.3 | 97.5 | 100 |
| Irradiation, 2 mins. | 86.0 | 91.9 | 95.1 | 97.6 | 100 |
| Irradiation, 3 mins. | 88.0 | 94.4 | 96.7 | 98.6 | 100 |
| Fiber Grade Specification | 70 | 90 | — | 95 | 98 |

EXAMPLE 3

In order to determine the effect of prolonged ultraviolet irradiation of glycol at the more energetic wave lengths i.e., below about 220 nanometers, on aldehyde formation, a standard 1-liter graduated cylinder was filled to a depth of about 425 centimeters with monoethylene glycol. The cylinder was flushed with nitrogen and provided with a tight-fitting plastic cover having apertures for the accommodation of a quartz immersion well and a sample withdrawal tube. A low pressure, 8 watt, mercury vapor lamp was turned-on, warmed-up for about 10 minutes and inserted into the immersion well, the glycol being continuously stirred via a magnetic stirrer. The glycol was irradiated for 4 hours with a sample being taken after 2 hours irradiation. The untreated and irradiated samples were submitted for analysis to determine their respective aldehyde contents with the following results:

|  | Aldehyde Content ppm Acetaldehyde |
| --- | --- |
| Untreated | 24 |
| 2 hrs. Irradiation | 164 |
| 4 hrs. Irradiation | 708 |

EXAMPLE 4

The procedure of Example 3 was followed except that the quartz immersion well was replaced by a Vycor ® immersion well. After 4 hours' irradiation, the aldehyde content of the glycol was found to be 14 ppm expressed as acetaldehyde.

We claim:

1. A process for treating ethylene glycol containing ultraviolet absorbing impurities so as to improve the ultraviolet light transmittance characteristics of the ethylene glycol at wavelengths in the range of 220 to 350 nanometers by irradiating the ethylene glycol with ultraviolet radiation, at a wavelength not less than 220 nanometers, from a controllable ultraviolet radiation emission source for a time sufficient to obtain ethylene glycol having ultraviolet light transmittance characteristics suitable for use in the manufacture of polyester fibers.

2. The process of claim 1 wherein the ethylene glycol is irradiated with ultraviolet light at a wavelength of at least 240 nanometers.

3. The process of claim 1 wherein the source of ultraviolet radiation is at least one high or low pressure mercury vapor lamp.

4. The process of claim 1 wherein the treated ethylene glycol has ultraviolet light transmittances of at least 70, 90, 95 and 98 percent at wavelengths of 220, 250, 275 and 350 nanometers, respectively.

* * * * *